(12) United States Patent
Sothen et al.

(10) Patent No.: US 9,233,888 B2
(45) Date of Patent: Jan. 12, 2016

(54) PROCESS FOR PRODUCING CYCLOHEXYLBENZENE

(71) Applicant: ExxonMobil Chemical Patents Inc., Baytown, TX (US)

(72) Inventors: Ryan A. Sothen, Houston, TX (US); Francisco M. Benitez, Cypress, TX (US); Charles Morris Smith, Princeton, NJ (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/416,929

(22) PCT Filed: Jul. 9, 2013

(86) PCT No.: PCT/US2013/049713
§ 371 (c)(1),
(2) Date: Jan. 23, 2015

(87) PCT Pub. No.: WO2014/028139
PCT Pub. Date: Feb. 20, 2014

(65) Prior Publication Data
US 2015/0203419 A1    Jul. 23, 2015

Related U.S. Application Data

(60) Provisional application No. 61/682,942, filed on Aug. 14, 2012.

(30) Foreign Application Priority Data

Sep. 17, 2012   (EP) ..................................... 12184657

(51) Int. Cl.
| C07C 45/53 | (2006.01) |
| C07C 37/08 | (2006.01) |
| C07C 2/66 | (2006.01) |
| C07C 2/70 | (2006.01) |
| C07C 2/74 | (2006.01) |
| C07C 407/00 | (2006.01) |
| C07C 6/12 | (2006.01) |
| C07C 7/12 | (2006.01) |
| C07C 4/18 | (2006.01) |
| C07C 45/00 | (2006.01) |

(52) U.S. Cl.
CPC ... *C07C 2/70* (2013.01); *C07C 2/74* (2013.01); *C07C 4/18* (2013.01); *C07C 6/126* (2013.01); *C07C 7/12* (2013.01); *C07C 37/08* (2013.01); *C07C 45/00* (2013.01); *C07C 45/53* (2013.01); *C07C 407/00* (2013.01); *C07C 2101/14* (2013.01); *C07C 2529/08* (2013.01); *C07C 2529/70* (2013.01); *C07C 2529/82* (2013.01)

(58) Field of Classification Search
CPC ............ C07C 45/53; C07C 37/08; C07C 2/66
USPC ........................... 568/342, 347, 798; 585/467
See application file for complete search history.

(56) References Cited

U.S. PATENT DOCUMENTS

| 4,094,918 | A | 6/1978 | Murtha et al. |
| 4,122,125 | A | 10/1978 | Murtha et al. |
| 4,177,165 | A | 12/1979 | Murtha et al. |
| 4,206,082 | A | 6/1980 | Murtha et al. |
| 5,053,571 | A | 10/1991 | Makkee |
| 6,037,513 | A | 3/2000 | Chang et al. |
| 6,313,362 | B1 * | 11/2001 | Green et al. .................. 585/323 |
| 6,489,529 | B1 | 12/2002 | Cheng et al. |
| 7,154,014 | B1 | 12/2006 | Negiz et al. |

FOREIGN PATENT DOCUMENTS

| WO | WO 98/07673 | 2/1998 |
| WO | WO 00/35836 | 6/2000 |
| WO | WO 2009/021604 | 2/2009 |
| WO | WO 2010/138248 | 12/2010 |
| WO | WO2010/138248 A2 * | 12/2010 |
| WO | WO 2011/115704 | 9/2011 |

* cited by examiner

*Primary Examiner* — Sikarl Witherspoon
(74) *Attorney, Agent, or Firm* — Siwen Chen; Stephen A. Baehl

(57) ABSTRACT

In a process for producing cyclohexylbenzene, benzene is reacted with cyclohexene under alkylation conditions effective to produce an alkylation effluent comprising cyclohexylbenzene and a polycyclohexylbenzene. A first feed comprising at least a portion of the alkylation effluent is then fed to a first separation device, where the first feed is separated into at least a first fraction containing cyclohexylbenzene and a second fraction containing the polycyclohexylbenzene, the second fraction also comprising an oxygenated hydrocarbon. At least a portion of the oxygenated hydrocarbon is removed from at least a portion of the second fraction in a second separation device to obtain a second feed. The second feed may then be reacted in a transalkylation or dealkylation reactor to convert at least part of the polycyclohexylbenzene to additional cyclohexylbenzene.

19 Claims, No Drawings

PROCESS FOR PRODUCING CYCLOHEXYLBENZENE

I. PRIORITY CLAIM

This application is a National Stage Application of International Application No. PCT/US2013/049713 filed Jul. 9, 2013, which claims the benefit of U.S. Provisional Application No. 61/682,942, filed Aug. 14, 2012, and European Application No. 12184657.0, filed Sep. 17, 2012, the disclosures of which are fully incorporated herein by their reference.

FIELD

The present invention relates to a process for producing cyclohexylbenzene. In particular, the present invention relates to a process for producing cyclohexylbenzene by alkylating benzene with cyclohexene where polycyclohexylbenzene is produced. The present invention is useful, e.g., in producing cyclohexylbenzene by hydroalkylation of benzene, which is subsequently used for making phenol and/or cyclohexanone.

BACKGROUND

Cyclohexylbenzene is a product of increasing importance in the chemical industry since it offers an alternative route to the Hock process for the production of phenol. The Hock process is a three-step process in which benzene is alkylated with propylene to produce cumene, the cumene is oxidized to the corresponding hydroperoxide, and then the hydroperoxide is cleaved to produce equimolar amounts of phenol and acetone.

Oxidation of cyclohexylbenzene has potential as an alternative route for the production of phenol since it co-produces cyclohexanone, which has a growing market and is used as an industrial solvent, as an activator in oxidation reactions and in the production of adipic acid and cyclohexanone resins. However, this alternative route requires the development of a commercially viable process for producing the cyclohexylbenzene precursor.

It has been known for many years that cyclohexylbenzene can be produced from benzene either directly by alkylation with cyclohexene or by the process of hydroalkylation or reductive alkylation. In the latter process, benzene is reacted with hydrogen in the presence of a catalyst such that the benzene undergoes partial hydrogenation to produce cyclohexene which then alkylates the benzene starting material. Thus, U.S. Pat. Nos. 4,094,918 and 4,177,165 disclose hydroalkylation of aromatic hydrocarbons over catalysts which comprise nickel and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low particularly at economically viable benzene conversion rates and large quantities of unwanted by-products were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt, and mixtures thereof and the contacting is conducted at a temperature of about 50° C. to 350° C., a pressure of about 100 kPa to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the hydroperoxide decomposed to the desired phenol and cyclohexanone.

However, although the use of MCM-22 family catalysts has significantly increased product selectivity, the manufacture of cyclohexylbenzene both by direct alkylation and by benzene hydroalkylation still tends to be accompanied by the co-production of significant quantities of by-products. One category of the by-products is polycyclohexylbenzenes, which can constitute up to 20 wt % of the conversion products. Thus, for the overall process to be economically feasible, it is highly desired to convert these polycyclohexylbenzenes into additional useful monocyclohexylbenzene product.

One possible method of converting polycyclohexylbenzenes into additional monocyclohexylbenzene is by transalkylation with additional benzene, a solution which is addressed in the '513 patent by effecting the transalkylation in the presence of a catalyst containing a molecular sieve the same as or similar to the one used in the hydroalkylation catalyst, namely an MCM-22 family catalyst, but in the absence of the metal components on the hydroalkylation catalyst and in the absence of a hydrogen co-feed. Other transalkylation processes are described in U.S. Pat. No. 6,489,529 and our co-pending PCT Application Nos. PCT/EP2008/006072 and PCT/US2010/031029.

Another process for producing additional cyclohexylbenzene from by-product polycyclohexylbenzenes is described in co-assigned, co-pending PCT Application No. PCT/2011/023537 and comprises dealkylation of the polycyclohexylbenzenes in the presence of an acid catalyst, such as at least one aluminosilicate, aluminophosphate, or silicoaluminophosphate.

The above methods of converting polycyclohexylbenzenes into additional useful monocyclohexylbenzene product require initial separation of the polycyclohexylbenzenes from the remainder of the alkylation or hydroalkylation process effluent. In certain embodiments, this is effected by a multi-stage fractionation process, in which unreacted benzene and cyclohexylbenzene product are removed from the process effluent in sequential fractionation stages leaving a $C_{12}+$ fraction containing the polycyclohexylbenzenes. Optionally, the $C_{12}+$ fraction is further fractionated to purge a heavies stream from the polycyclohexylbenzenes. Currently, in order to achieve satisfactory separation, each fractionation stage is operated under vacuum and at a relatively high temperature. In a commercial setting, vacuum operation is likely to result in air ingress and hence formation of oxygenated hydrocarbons. Not only can this lead to loss of valuable product but also the oxygenated hydrocarbons may deactivate the catalyst employed in the downstream transalkylation or dealkylation of the polycyclohexylbenzenes.

According to the invention, it has now been found that removal of oxygenated hydrocarbons from a fraction rich in polycyclohexylbenzenes separated from the effluent from the reaction of benzene with cyclohexene inhibits deactivation of the catalyst employed in the downstream transalkylation or dealkylation of the polycyclohexylbenzenes.

SUMMARY

In one aspect, the invention resides in a process for producing cyclohexylbenzene, the process comprising:

(a) reacting benzene with cyclohexene under alkylation conditions effective to produce an alkylation effluent comprising cyclohexylbenzene and a polycyclohexylbenzene;

(b) supplying a first feed comprising at least a portion of the alkylation effluent from step (a) to a first separation device;

(c) separating the first feed in the first separation device into at least a first fraction containing cyclohexylbenzene at a concentration higher than the first feed and a second fraction containing the polycyclohexylbenzene at a concentration higher than the first feed, the second fraction also comprising an oxygenated hydrocarbon; and (d) removing at least a portion of the oxygenated hydrocarbon from at least a portion of the second fraction in a second separation device to obtain a second feed having a reduced oxygenated hydrocarbon concentration than the second fraction.

In certain embodiments, step (d) comprises use of an adsorbent, such as alumina.

In one embodiment, the cyclohexene is generated in step (a) by hydrogenation of benzene in situ. In certain embodiments, step (a) is conducted in the presence of a catalyst comprising a hydrogenating metal component and an alkylating acid component such as a solid acid component.

Typically, the process further comprises contacting at least a portion of the second feed with benzene in a transalkylation reactor in the presence of a transalkylation catalyst under transalkylation conditions to produce a transalkylation effluent comprising cyclohexylbenzene. In certain embodiments, the transalkylation catalyst comprises an acid, such as a solid acid, e.g., faujasite. The transalkylation conditions typically comprise a temperature in a range from 300° F. to 400° F. (149° C. to 204° C.) and an absolute pressure of at least 185 psi (1275 kPa) such that at least a portion of the benzene is in a liquid phase.

Alternatively, the process further comprises contacting at least a portion of the second feed in a dealkylation reactor in the presence of a dealkylation catalyst under dealkylation conditions to produce a dealkylation effluent comprising cyclohexylbenzene and cyclohexene and/or cyclohexane.

In certain embodiments, the oxygenated hydrocarbon is selected from a ketone, an alcohol, an aldehyde, a carboxylic acid, and combinations of two or more thereof. Typically, the oxygenated hydrocarbon has a concentration in the second fraction separated in step (c) of at least 1 ppm and a concentration in the second feed obtained in step (d) of at most 1 wt %.

In a further aspect, the invention resides in a process for producing phenol and/or cyclohexanone, the process comprising:

(a) reacting benzene with cyclohexene under alkylation conditions effective to produce an alkylation effluent comprising cyclohexylbenzene and a polycyclohexylbenzene;

(b) supplying a first feed comprising at least a portion of the alkylation effluent from step (a) to a first separation device;

(c) separating the first feed in the first separation device into at least a first fraction containing cyclohexylbenzene at a concentration higher than the first feed and a second fraction containing the polycyclohexylbenzene at a concentration higher than the first feed, the second fraction also comprising an oxygenated hydrocarbon;

(d) removing at least a portion of the oxygenated hydrocarbon from at least a portion of the second fraction in a second separation device to obtain a second feed having a reduced oxygenated hydrocarbon concentration than the second fraction;

(e) converting at least part of the polycyclohexylbenzene in the second feed by delkylation or transalkylation to cyclohexylbenzene;

(f) oxidizing at least part of the cyclohexylbenzene from (a) and/or (e) to produce cyclohexylbenzene hydroperoxide; and (g) cleaving at least part of the cyclohexylbenzene hydroperoxide from (f) to produce phenol and cyclohexanone.

DETAILED DESCRIPTION

In the present disclosure, a process may be described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two or more hydrogenating metals are used, unless specified to the contrary or the context clearly indicates that only one hydrogenating metal is used. Likewise, "an oxygenated hydrocarbon" should be interpreted to include one or more types of hydrogenated hydrocarbon at various concentrations unless specified or indicated by the context to mean only one specific type of hydrogenated hydrocarbon.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzne, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene, 1,3,5-tricyclohexylbenzene, and combinations and mixtures thereof at any proportion. The generic term "polycycloyhexylbenzene" shall include any of the dicyclohexylbenzene isomers and tricyclohexylbenzene isomers described above, and combinations and mixtures of at least two thereof in any proportion.

The process described herein relates to the production of cyclohexylbenzene by the alkylation of benzene with cyclohexene according to the following reaction:

The cyclohexene can be supplied to the reaction zone as a separate feed from the benzene, but normally is produced in situ by the selective hydrogenation of benzene in the presence of a bifunctional catalyst. Such a reaction is generally termed "hydroalkylation" and may be summarized as follows:

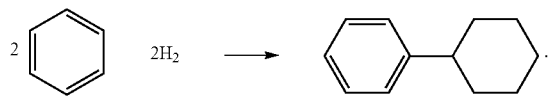 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is desirable that the hydrogen is at least 99 wt % pure.

In certain embodiments, the total feed to the hydroalkylation step contains less than 1000 ppm, such as less than 500 ppm, for example less than 100 ppm, water. In addition, the total feed can contain less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but is advantageously arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Desirably the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, in certain embodiments the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a hydrogenating metal component and an alkylating acid component. The acid component is advantageously a solid acid. In certain embodiments, the alkylating acid component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. In certain embodiments, the amount of hydrogenating metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenating metal present is such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 family molecular sieve by, for example, impregnation or ion exchange. However, in a more preferred embodiment, at least 50 wt %, for example at least 75 wt %, and in certain embodiments substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide, in certain embodiments by impregnation, before the metal-containing inorganic oxide is composited with the molecular sieve. Desirably, the catalyst composite is produced by co-pelletization, in which a mixture of the molecular sieve and the metal-containing inorganic oxide are formed into pellets at high pressure (in certain embodiments about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 family zeolite catalyst is highly selective towards cyclohexylbenzene, the effluent from the hydroalkylation reaction may contain some polycyclohexylbenzene by-product, especially one or more of 1,3-dicyclohexylbenzene and 1,4-dicylcohexylbenzene. To improve product yields, the polycyclohexylbenzene by-product is separated from the hydroalkylation reaction effluent and transalkylated or dealkylated in the presence of an acid catalyst to produce additional monocyclohexylbenzene.

Separation of the polycyclohexylbenzene from the hydroalkylation reaction effluent can be effected in any known separation device but is in certain embodiments conducted by fractionation. In certain particular embodiments, the hydroalkylation reaction effluent is supplied to a fractionation train including an optional benzene column, in which residual, unreacted benzene is initially separated from the alkylation effluent and recycled back to the hydroalkylation reaction. After removal of the unreacted benzene, the remainder of the hydroalkylation reaction effluent is fed to a further fractionation column where the effluent is separated into a first fraction containing cyclohexylbenzene and a second fraction containing the polycyclohexylbenzenes. The further fractionation column may be operated at or above atmospheric pressure, such as from 100 kPa to 300 kPa. More preferably, however, the further fractionation column is operated at sub-atmospheric pressure, that is below 100 kPa. In certain embodiments, the further fractionation column is operated such that the concentration of cyclohexylbenzene in the second fraction is at most 10 wt %, in certain embodiments at most 8 wt %, in certain other embodiments at most 5 wt %, in certain embodiments at most 3 wt %, and in certain other embodiments at most 1 wt %.

Particularly when operated at sub-atmospheric pressure, it is difficult to prevent oxygen ingress into the further fractionation column. Such oxygen reacts with the hydroalkylation reaction effluent to produce heavier oxygenated hydrocarbons, such as ketones, alcohols, aldehydes, and carboxylic acids. These oxygenated hydrocarbons partition to the bottom of the fractionation column with the polycyclohexylbenzenes such that the second fraction may contain at least 1 ppm, in certain embodiments at least 10 ppm, in certain embodiments at least 100 ppm, in certain embodiments at least 1000 ppm, in certain embodiments at least 2000 ppm, in certain embodiments at least 4000 ppm, in certain embodiments at least 6000 ppm, in certain embodiments at least 8000 ppm, in certain other embodiments at least 1 wt % of oxygenated hydrocarbons.

The acid catalyst (such as a solid acid) employed in a subsequent transalkylation or dealkylation reaction to convert the polycyclohexylbenzene in the second fraction to cyclohexylbenzene is readily deactivated by oxygenates. Thus, before being supplied to the transalkylation or dealkylation reactor, the second fraction is treated to reduce the level of oxygenated hydrocarbons to obtain a second feed. The second feed typically comprises at most 1 wt %, in certain embodiments at most 8000 ppm by weight, in certain embodiments at most 6000 ppm, in certain embodiments at most 4000 ppm, in certain embodiments at most 2000 ppm, in certain embodiments at most 1000 ppm, in certain embodiments at most 800 ppm, in certain embodiments at most 500 ppm, in certain embodiments at most 400 ppm, in certain embodiments at most 200 ppm, in certain embodiments at most 100 ppm, in certain embodiments at most 80 ppm, in certain embodiments at most 60 ppm, in certain embodiments at most 50 ppm, in certain embodiments at most 40 ppm, in certain embodiments at most 20 ppm, in certain embodiments at most 10 ppm, in certain embodiments at most 8 ppm, in certain embodiments at most 5 ppm, in certain embodiments at most 3 ppm, in certain embodiments at most 1 ppm, by weight of the second feed. A suitable method of reducing the oxygenate level to the desired value is by passage of the second fraction through an adsorbent. Suitable adsorbents include molecular sieves, such as 13×, Clinoptilolite, and metal oxides, such as alumina (e.g., Selexsorb® CDX by BASF), and copper oxide (e.g., Puristar, by BASF).

In one embodiment, after treatment to reduce the level of oxygenate impurities, the second feed is fed to a transalkylation reactor, separate from the hydroalkylation reactor, where the second feed is contacted with benzene in the presence of acid transalkylation catalyst, such as a molecular sieve of the MCM-22 family, zeolite beta, MCM-68 (see U.S. Pat. No. 6,014,018), faujasite, or mordenite. Faujasite is the preferred solid acid catalyst for the transalkylation reaction. Typically, the transalkylation reaction is conducted under conditions which are sufficient to maintain at least a portion of the benzene in a liquid phase and which suitably include a temperature from 300° F. to 400° F. (149° C. to 204° C.), such as from 330° F. to 385° F. (166° C. to 196° C.), an absolute pressure of at least 185 psi (1275 kPa), such as at least 200 psi (1369 kPa), a weight hourly space velocity of about 1 to about 10 hr$^{-1}$ on total feed, and a benzene/polycyclohexylbenzene weight ratio about of 1:1 to about 5:1. Under these conditions, benzene reacts with the polycyclohexylbenzenes in the second feed to produce a transalkylation effluent comprising cyclohexylbenzene.

The transalkylation effluent is then fed to a fractionation train, preferably the same fractionation train used to separate the hydroalkylation effluent, so as to remove residual benzene for recycle to the transalkylation or hydroalkylation reactor and to recover the cyclohexylbenzene.

In another embodiment, after treatment to reduce the level of oxygenate impurities, the second feed is fed to a dealkylation reactor, separate from the hydroalkylation reactor, such as a reactive distillation unit. Typically, the delakylation reactor contains a solid acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia, and mixtures thereof. In certain embodiments, the acid catalyst includes at least one aluminosilicate, aluminophosphate or silicoaluminophosphate of the FAU, AEL, AFI, and MWW family.

Unlike transalkylation, which in certain embodiments is conducted in a molar excess of additional benzene, the dealkylation reaction can be conducted in the absence of added benzene. In some cases, however, it may be desirable to add benzene to the dealkylation reaction to reduce coke formation, in which case the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen can be introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

The conditions employed in the dealkylation reaction are not narrowly confined but in certain embodiments include a temperature of about 150° C. to about 500° C. and a pressure of 15 psig to 500 psig (200 kPa to 3550 kPa).

The main reaction occurring in the dealkylation reaction is summarized below:

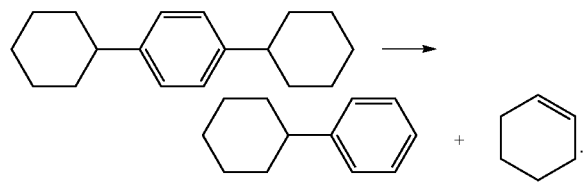

Thus, in addition to monocyclohexylbenzene, the product of the dealkylation reaction contains cyclohexene and/or, if hydrogen is present, cyclohexane normally together with unreacted poly-cyclohexylbenzenes. The dealkylation reaction product is therefore fed to a fractionation train, preferably the same fractionation train used to separate the hydroalkylation effluent. In the fractionation train, the cyclohexene and/or cyclohexane are initially removed from the dealkylation product and recycled to the hydroalkylation unit with the unreacted benzene from the hydroalkylation effluent. In the hydroalkylation unit, the recycled cyclohexene will react with benzene forming cyclohexylbenzene and/or poly-cyclohexylbenzenes.

The cyclohexylbenzene produced by the present process can be used as an intermediate in the production of pharmaceuticals, but is particularly intended for conversion to phenol and cyclohexanone. Such a process involves oxidation of the cyclohexylbenzene to the corresponding hydroperoxide and then acid cleavage of the hydroperoxide to the desired phenol and cyclohexanone.

Oxidation of the cyclohexylbenzene is accomplished by contacting the cyclohexylbenzene with an oxygen-containing gas in the presence of a catalyst. The oxygen-containing gas can be air, or a derivative of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetra-bromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, e.g., by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. In certain embodiments, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 Å molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Cleavage of the cyclohexyl-1-phenyl-1-hydroperoxide produced in the oxidation step into phenol and cyclohexanone is conducted in the presence of an acid catalyst.

In certain embodiments, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to no greater than 2000 wppm of the acid catalyst, or at least 300 wppm to no greater than 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. In certain embodiments, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction, but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

In certain embodiments, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove heat generated.

The product of the cleavage reaction is desirably a substantially equimolar mixture of phenol and cyclohexanone.

The invention will now be more particularly described with reference to the following non-limiting examples.

EXAMPLE 1

Comparative

After removal of residual benzene, the effluent from a benzene hydroalkylation process was fractionated at atmospheric pressure to produce a transalkylation feed comprising a mixture of cyclohexylbenzene (CHB) and dicyclohexylbenzene (DiCHB) isomers. The resultant feed was supplied to a transalkylation reactor having an inlet temperature of 335° F. (168° C.) and a backpressure of 200 psig (1379 kPa gauge). Benzene was also supplied to the transalkylation reactor. The supply rate of the transalkylation feed was 75 grams per hour and the weight ratio of benzene to polycyclohexyl benzenes (including DiCHB and TriCHB) supplied to the reactor was 4:1. The conversions of the DiCHB (including 1,3-DiCHB and 1,4-DiCHB) across the reactor was approximately 60% overall. The results were stable over a five day period.

EXAMPLE 2

Comparative

After removal of residual benzene, the effluent from a benzene hydroalkylation process was fractionated at sub-atmospheric pressure, less than 1.5 psig (10 kPa), to produce a polycyclohexyl benzene composed mainly of DiCHB (CHB content less than 10 wt %). The DiCHB feed was treated with a Selexsorb CDO adsorbent bed before entering the transalkylation reactor. The transalkylation reactor was again operated at an inlet temperature of 335° F. (168° C.) and a backpressure of 200 psig (1379 kPa guage). The supply rate of the transalkylation feed was 75 grams per hour and the weight ratio of benzene to DiCHB supplied to the reactor was 3:1. The conversions of the DiCHB (including 1,3-DiCHB and 1,4-DiCHB) across the faujasite catalyst was about 73%. Since there is little CHB in the inlet feed, the reactor is able to achieve a higher conversion of the DiCHB's than in Example 1. The results were stable over a two day period.

EXAMPLE 3

The process of Example 2 was conducted and at the end of the two day period the adsorbent bed was removed from the process while the transalkylation reactor conditions and feeds of Example 2 were maintained. The conversion of the dialkylate steadily declined to 30% for the DiCHB (including 1,3-DiCHB and 1,4-DiCHB) over the course of five days. The decline demonstrated no sign of slowing down before the reactor was taken offline.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising:
    (a) reacting benzene with cyclohexene under alkylation conditions effective to produce an alkylation effluent comprising cyclohexylbenzene and a polycyclohexylbenzene;
    (b) supplying a first feed comprising at least a portion of the alkylation effluent from step (a) to a first fractionation column;
    (c) separating the first feed in the first fractionation column into at least a first fraction containing cyclohexylbenzene at a concentration higher than the first feed and a second fraction containing the polycyclohexylbenzene at a concentration higher than the first feed,
        wherein an oxygenated hydrocarbon is formed in the first fractionation column, such that the second fraction also comprises the oxygenated hydrocarbon;
    (d) passing the second fraction through an adsorbent selected from the group consisting of alumina and copper oxide, thereby obtaining a second feed having a reduced oxygenated hydrocarbon concentration as compared to the second fraction; and
    (e) contacting the second feed with benzene in a transalkylation reactor in the presence of a transalkylation catalyst under transalkylation conditions to produce a transalkylation effluent comprising cyclohexylbenzene.

2. The process of claim 1, wherein the fractionation column is operated at a pressure less than 100 kPa.

3. The process of claim 1, wherein step (a) is conducted in the presence of a catalyst comprising a hydrogenating metal component and an alkylating acid component.

4. The process of claim 3, wherein the alkylating acid component comprises a zeolite of the MCM-22 family.

5. The process of claim 1, wherein in step (a), the alkylation effluent comprises residual benzene, and at least a portion of the residual benzene is separated from the alkylation effluent and recycled back to step (a).

6. The process of claim 1, wherein the transalkylation catalyst comprises faujasite.

7. The process of claim 1 wherein in step (e), the transalkylation conditions comprise a temperature in a range from 149° C. to 204° C.

8. The process of claim 1, wherein in step (e), the transalkylation conditions are such as to maintain at least a portion of the benzene in a liquid phase.

9. The process of claim 1 wherein in step (e), the transalkylation conditions comprise an absolute pressure of at least 1275 kPa.

10. The process of claim 1, the process further comprising:
    (f) separating at least a portion of the transalkylation effluent into at least a fraction containing cyclohexylbenzene and a fraction containing a polycyclohexylbenzene.

11. The process of claim 10, wherein said portion of the transalkylation effluent is included in the first feed of step (b) and said separating in step (f) is conducted in said first fractionation column of step (c).

12. The process of claim 1, further comprising:
    (g) contacting at least a portion of the second feed in a dealkylation reactor in the presence of a dealkylation catalyst under dealkylation conditions to produce a dealkylation effluent comprising cyclohexylbenzene.

13. The process of claim 1, wherein the second fraction in step (c) has an oxygenated hydrocarbon concentration of at least 1 ppm by weight.

14. The process of claim 1, wherein the second feed in step (d) has an oxygenated hydrocarbon concentration of at most 1 wt %.

15. The process of claim 1, wherein the concentration of cyclohexylbenzene in the second feed is at most 10 wt %.

16. The process of claim 1, further comprising:
(f) oxidizing at least part of the cyclohexylbenzene from (a) and/or (e) to produce cyclohexylbenzene hydroperoxide; and
(g) cleaving at least part of the cyclohexylbenzene hydroperoxide from (f) to produce phenol and cyclohexanone.

17. The process of claim 16, wherein step (d) comprises use of an alumina adsorbent.

18. The process of claim 1, wherein the fractionation column is operated at a pressure less than 100 kPa.

19. The process of claim 16, wherein step (a) is conducted in the presence of a catalyst comprising a hydrogenating metal component and an alkylating acid component.

* * * * *